United States Patent
Nygaard

(10) Patent No.: US 9,047,657 B2
(45) Date of Patent: Jun. 2, 2015

(54) METHOD AND SYSTEM FOR OPTICALLY INSPECTING OUTER PERIPHERAL SURFACES OF PARTS

(71) Applicant: GII Acquisition, LLC, Davisburg, MI (US)

(72) Inventor: Michael G. Nygaard, Fenton, MI (US)

(73) Assignee: GII ACQUISITION, LCC, Davisburg, MI (US)

( * ) Notice: Subject to any disclaimer, the term of this patent is extended or adjusted under 35 U.S.C. 154(b) by 28 days.

(21) Appl. No.: 13/873,293

(22) Filed: Apr. 30, 2013

(65) Prior Publication Data
US 2013/0258046 A1    Oct. 3, 2013

Related U.S. Application Data

(63) Continuation-in-part of application No. 13/109,369, filed on May 17, 2011, now Pat. No. 8,570,504.

(51) Int. Cl.
| | | |
|---|---|---|
| *G01N 21/00* | (2006.01) | |
| *G01N 21/86* | (2006.01) | |
| *G06T 7/00* | (2006.01) | |

(Continued)

(52) U.S. Cl.
CPC ............... *G06T 7/0004* (2013.01); *B07C 5/342* (2013.01); *F42B 35/00* (2013.01); *G01N 21/9515* (2013.01); *G01N 21/952* (2013.01); *G01N 21/909* (2013.01); *B07C 2501/0009* (2013.01)

(58) Field of Classification Search
USPC ...................... 356/237.1–241.6, 242.1–243.8, 356/426–431, 600–640
See application file for complete search history.

(56) References Cited

U.S. PATENT DOCUMENTS

| | | | | |
|---|---|---|---|---|
| 3,411,009 A | * | 11/1968 | Ford et al. | ................. 250/223 B |
| 3,924,953 A | | 12/1975 | Allard | |

(Continued)

FOREIGN PATENT DOCUMENTS

| | | |
|---|---|---|
| WO | 2005022076 A2 | 3/2005 |
| WO | 2009130062 A1 | 10/2009 |

OTHER PUBLICATIONS

International Search Report and Written Opinion; International Application No. PCT/US2012/037892; date of mailing Jul. 27, 2012.

(Continued)

*Primary Examiner* — Kara E Geisel
*Assistant Examiner* — Jarreas C Underwood
(74) *Attorney, Agent, or Firm* — Brooks Kushman P.C.

(57) ABSTRACT

A method and system for optically inspecting the entire outer peripheral surface of a part are provided. The system includes an enclosure which allows movement of a part relative to the enclosure both prior to and after inspection within the enclosure. An illumination assembly simultaneously illuminates a plurality of exterior side surfaces of the part which are annularly spaced about the axis of the part with radiation when the part is at a predetermined location within the enclosure to obtain corresponding reflected radiation signals. A plurality of lens and detector assemblies are provided. Each of the assemblies forms an optical image of one of the illuminated exterior side surfaces from the reflected radiation signals and detects the formed optical image within the enclosure. A processor processes the detected optical images to obtain a continuous, seamless, 360° panoramic composite image of the peripheral surface of the part.

24 Claims, 6 Drawing Sheets

(51) Int. Cl.
*B07C 5/342* (2006.01)
*F42B 35/00* (2006.01)
*G01N 21/95* (2006.01)
*G01N 21/952* (2006.01)
*G01N 21/90* (2006.01)

(56) References Cited

U.S. PATENT DOCUMENTS

| | | | |
|---|---|---|---|
| 4,280,624 A * | 7/1981 | Ford | 209/524 |
| 4,315,688 A | 2/1982 | Pryor | |
| 4,547,674 A | 10/1985 | Pryor et al. | |
| 4,598,998 A | 7/1986 | Kamei et al. | |
| 4,636,635 A * | 1/1987 | Kronseder | 250/223 B |
| 4,644,394 A | 2/1987 | Reeves | |
| 4,691,231 A * | 9/1987 | Fitzmorris et al. | 348/127 |
| 4,721,388 A | 1/1988 | Takagi et al. | |
| 4,831,251 A | 5/1989 | Hanna | |
| 4,852,983 A | 8/1989 | Fein | |
| 4,906,098 A | 3/1990 | Thomas et al. | |
| 4,912,318 A * | 3/1990 | Kajiura et al. | 250/223 B |
| 4,923,066 A * | 5/1990 | Ophir et al. | 209/538 |
| 4,969,746 A * | 11/1990 | McConnell et al. | 356/601 |
| 4,970,401 A | 11/1990 | Sadeh et al. | |
| 4,983,043 A | 1/1991 | Harding | |
| 5,012,117 A | 4/1991 | Karafa et al. | |
| 5,164,995 A | 11/1992 | Brooks et al. | |
| 5,168,458 A | 12/1992 | Gomes | |
| 5,170,306 A | 12/1992 | Gomes | |
| 5,291,272 A | 3/1994 | Demisu | |
| 5,383,021 A | 1/1995 | Hanna | |
| 5,521,707 A | 5/1996 | Castore et al. | |
| 5,568,263 A | 10/1996 | Hanna | |
| 5,608,530 A | 3/1997 | Gates | |
| 5,646,724 A | 7/1997 | Hershline | |
| 5,975,710 A | 11/1999 | Luster | |
| 6,038,521 A * | 3/2000 | Kanai | 702/121 |
| 6,055,329 A | 4/2000 | Mufti | |
| 6,252,661 B1 | 6/2001 | Hanna | |
| 6,285,034 B1 * | 9/2001 | Hanna et al. | 250/559.2 |
| 6,289,600 B1 | 9/2001 | Watts | |
| 6,313,948 B1 | 11/2001 | Hanna | |
| 6,324,016 B1 | 11/2001 | Luster | |
| 6,525,333 B1 | 2/2003 | Hooker et al. | |
| 6,959,108 B1 | 10/2005 | Bartelt et al. | |
| 7,312,607 B2 | 12/2007 | Nygaard | |
| 7,329,855 B2 * | 2/2008 | Katayama et al. | 250/223 B |
| 7,403,872 B1 | 7/2008 | St. Onge et al. | |
| 7,633,046 B2 | 12/2009 | Spalding | |
| 7,633,634 B2 | 12/2009 | Spalding et al. | |
| 7,633,635 B2 | 12/2009 | Nygaard et al. | |
| 7,684,054 B2 | 3/2010 | Crowther | |
| 7,738,088 B2 | 6/2010 | Spalding | |
| 7,738,121 B2 * | 6/2010 | Spalding | 356/638 |
| 7,755,754 B2 | 7/2010 | Spalding | |
| 7,777,900 B2 | 8/2010 | Nygaard et al. | |
| 7,796,278 B2 | 9/2010 | Spalding et al. | |
| 7,812,970 B2 | 10/2010 | Nygaard | |
| 8,054,460 B2 | 11/2011 | Agapiou et al. | |
| 8,179,434 B2 | 5/2012 | Koval et al. | |
| 2003/0201211 A1 | 10/2003 | Bennett et al. | |
| 2004/0223143 A1 | 11/2004 | Ysuda et al. | |
| 2004/0263957 A1 * | 12/2004 | Hirahara et al. | 359/372 |
| 2005/0094867 A1 | 5/2005 | Jones, Jr. et al. | |
| 2005/0174567 A1 | 8/2005 | Hanna | |
| 2006/0236792 A1 | 10/2006 | Hanna | |
| 2008/0049235 A1 | 2/2008 | Crowther | |
| 2009/0278925 A1 * | 11/2009 | Koval et al. | 348/92 |
| 2010/0201806 A1 | 8/2010 | Nygaard et al. | |
| 2010/0245850 A1 | 9/2010 | Lee et al. | |

OTHER PUBLICATIONS

International Preliminary Report on Patentability; International application No. PCT/US2012/037892; date of issuance of report Nov. 19, 2013.

International Search Report and Written Opinion; International application No. PCT/US14/016390; date of mailing Dec. 8, 2014.

* cited by examiner

METHOD AND SYSTEM FOR OPTICALLY INSPECTING OUTER PERIPHERAL SURFACES OF PARTS

CROSS-REFERENCE TO RELATED APPLICATIONS

This application is a continuation-in-part application of U.S. patent application entitled "Method and System For Optically Inspecting Parts" filed May 17, 2011 and having U.S. Ser. No. 13/109,369.

TECHNICAL FIELD

This invention relates in general to the field of the non-contact, optical inspection of parts and, more particularly, to methods and systems for optically inspecting outer peripheral surfaces of parts, such as ammunition cases and threaded fasteners.

OVERVIEW

Traditional manual, gauging devices and techniques have been replaced to some extent by automatic inspection methods and systems. However, such automatic inspection methods and systems still have a number of shortcomings associated with them.

Many parts, such as fasteners and ammunition cartridges and cases develop cracks, splits, or other outer surface defects during the manufacturing process. While parts can be rotated about their axes during the inspection process, this adds additional time to the process.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

FIG. 1a is a side schematic view of a .50 caliber case. As explained in the above-noted military standard, a case is counted as a defective because of a split case if the cartridge case shows a definite separation of the metal entirely through the case wall. A case is classified as either a "major" or "critical" defect depending on the location of split. A split in the (I), (S) or (J) position is counted as a "major" defect when no loss of powder occurs; and as a "critical" defect when loss of powder occurs. A split in the (K), (L) or (M) position is counted as a "critical" defect.

FIG. 1b is a side schematic view of a .30 caliber case. As noted above, a case is counted as a defective because of a split case if the cartridge case shows a definite separation of the metal entirely through the case wall. A case is classified either as "major" or "critical" defective depending on location of split. A split in the (I) of (J) position is counted as a "major" defect when no loss of powder occurs; and as a "critical" defect when loss of powder occurs. A split in the (K), (L), or (M) position is counted as a "critical" defect.

FIG. 1c is a side schematic view of a .45 caliber case. Again, as noted above, a case is counted as defective because of a split case if the cartridge case shows a definite separation of the metal entirely through the case wall. A case is classified either as a "major" or "critical" defective depending on the location of the split. A split in the (I) or (J) position is counted as a "major" defect when no loss of powder occurs; and as a "critical" defect when loss of powder occurs. A split in the (K), (L), or (M) position is counted as a "critical" defect.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain trilobular parameters.

Other U.S. patent documents related to the invention include: U.S. Pat. Nos. 4,315,688; 4,598,998; 4,644,394; 4,852,983; 4,906,098; 5,521,707; 5,608,530; 5,646,724; 5,291,272; 6,055,329; 4,983,043; 3,924,953; 5,164,995; 4,721,388; 4,969,746; 5,012,117; 7,684,054; 7,403,872; 7,633,635; 7,312,607; 7,777,900; 7,633,046; 7,633,634; 7,738,121; 7,755,754; 7,738,088; 7,796,278; 7,684,054; 7,812,970; 8,054,460; 8,179,434 and U.S. published patent applications 2010/0245850 and 2010/0201806.

SUMMARY OF EXAMPLE EMBODIMENTS

An object of at least one embodiment of the present invention is to provide a high-speed, compact, low cost, method and system for optically inspecting the outer peripheral surfaces of parts.

In carrying out the above object and other objects of at least one embodiment of the present invention, a method of optically inspecting parts is provided. Each of the parts has a length, a width, an axis and an outer peripheral surface which extends 360° around the part. The method includes supporting a part to be inspected at an inspection station so that the part has a predetermined position and orientation for inspection. The method also includes supporting a plurality of angularly spaced radiation sources at the inspection station. The method further includes energizing the radiation sources so that the radiation sources simultaneously illuminate a plurality of exterior side surfaces of the part which are angularly spaced about the axis of the part at the inspection station to obtain corresponding reflected radiation signals. The method still further includes forming an optical image of each illuminated side surface from the reflected radiation signals at an image plane. The method includes detecting the optical images at the image planes to obtain a plurality of detected optical images. The method also includes processing the detected optical images to obtain a continuous, seamless, 360° panoramic composite image of the peripheral surface of the part.

The method may further include moving the part relative to the inspection station both prior to and after inspection.

The part may be substantially stationary or moving during inspection.

The method may further include the step of coordinating the inspection of the part at the inspection station with the relative movement of the part to and from the inspection station to control the relative movement and the inspecting of the part.

The method may further include processing the composite image to identify a defective part.

The method may further include processing the composite image to obtain a measurement of the part.

The radiation sources may be visible light sources.

The radiation may be LED or fluorescent radiation.

The parts may include cartridge cases and the method may further include processing the composite image of each case to determine at least one of a dent, a split, a perforation, a crack, a scratch, a wrinkle, a buckle, a bulge, and a surface blemish located at the side surfaces of each case.

The parts may include threaded fasteners and the method may further include processing the composite image of each fastener to determine a thread profile parameter. The method may further include processing each composite image to identify a thread defect.

Further in carrying out the above object and other objects of at least one embodiment of the present invention, a system for optically inspecting parts is provided. Each of the parts has a length, a width, an axis and an outer peripheral surface which extends 360° around the part. The system includes an enclosure which allows movement of a part relative to the enclosure both prior to and after inspection within the enclosure. An illumination assembly simultaneously illuminates a plurality of exterior side surfaces of the part which are annularly spaced about the axis of the part with radiation when the part is at a predetermined location within the enclosure to obtain corresponding reflected radiation signals. A plurality of lens and detector assemblies is also provided. Each of the assemblies forms an optical image of one of the illuminated exterior side surfaces from the reflected radiation signals and detects the formed optical image within the enclosure. A processor processes the detected optical images to obtain a continuous, seamless, 360° panoramic composite image of the peripheral surface of the part.

The system may further include a part transfer subsystem to transfer the part so that the part travels along a first path which extends into the enclosure and to transfer the part after inspection so that the inspected part travels along a second path which extends out of the enclosure.

Each of the lens and detector assemblies may include an image sensor having an image plane to detect optical images.

The radiation may be LED or fluorescent radiation.

The parts may include cartridge cases and the processor may process the composite image of each case to determine at least one of a dent, a split, a perforation, a crack, a scratch, a wrinkle, a buckle, a bulge, and a surface blemish located at the side surfaces of each case.

The parts may include threaded fasteners.

The processor may process the composite image to identify a thread profile parameter.

The processor may process the composite image to identify a thread defect.

The part transfer subsystem may include a conveyor or a movable table or disk.

Other technical advantages will be readily apparent to one skilled in the art from the following figures, descriptions and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is made to the following description taken in conjunction with the accompanying drawings, in which.

DETAILED DESCRIPTION OF EXAMPLE EMBODIMENTS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1C:
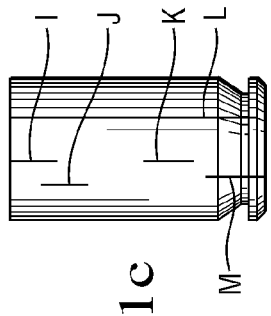
FIG. 1c is a side schematic view of a .45 caliber cartridge case.
Figure 2B:
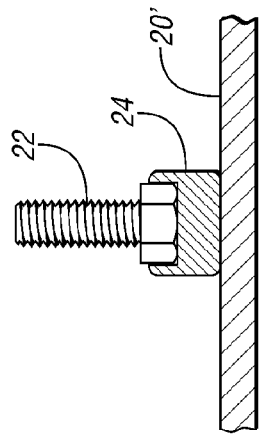
FIG. 2b is a side schematic view, partially broken away and in cross section, of a threaded fastener which head is received and retained within a chuck component or fixture which, in turn, is received and retained on a transfer mechanism.
Figure 1B:
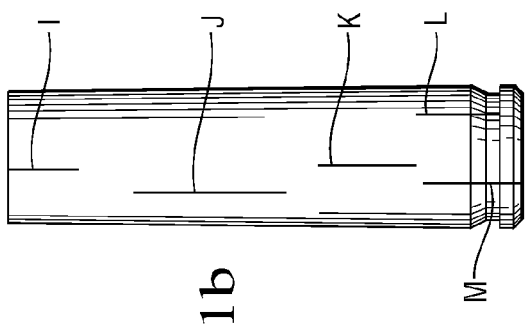
FIG. 1b is a side schematic view of a .30 caliber cartridge case.
Figure 2A:
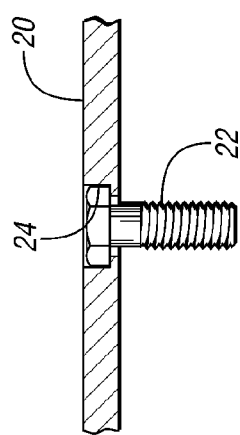
FIG. 2a is a side schematic view, partially broken away and in cross section, of a threaded fastener received and retained in a transfer mechanism.
Figure 1A:
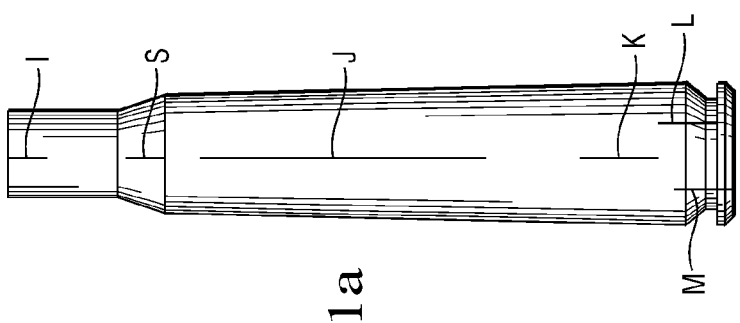
FIG. 1a is a side schematic view of a .50 caliber cartridge case.

FIG. 2a is a view of a transfer mechanism 20 for moving parts and from which a part such as a threaded fastener or bolt 22 hangs or is suspended from an aperture 24 in the transfer mechanism 20 at its head. In this way the threads of the bolt 22 are exposed for optical inspection by a system of at least one embodiment of the present invention. Other parts, such as the cases of FIGS. 1a-1c can be supported in a similar fashion.

FIG. 2b is a view of the threaded bolt 22 which is supported to stand on the upper surface of a transfer mechanism 20' by a chuck or fixture 24 mounted on the mechanism 20' at a fixed location thereon. The head of the bolt 22 is supported by and disposed within the fixture 24. This feature allows the threads of the bolt 22 to be optically inspected in another embodiment of a system of the present invention. Other parts, such as the cases of FIGS. 1a-1c can be supported in a similar fashion.

Figure 5:
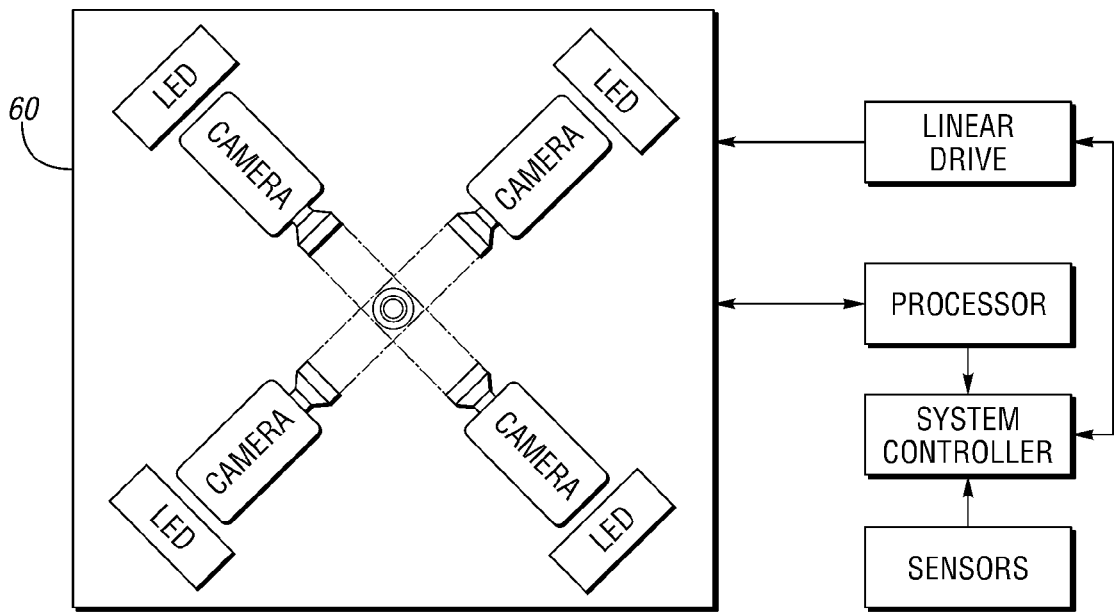
FIG. 5 is top schematic block diagram view of an enclosure, an illumination assembly, a plurality of lens and detector assemblies, an image processor and a system controller of at least one embodiment of the invention.

Generally, and as shown in FIG. 5, an illumination assembly and a plurality of lens and detector assemblies are mounted within an enclosure to provide multiple side imaging of parts. One aspect of one embodiment of the present invention relates to a novel method and configuration which uses a processor to process detected optical images to form a continuous, seamless, 360 degree panoramic composite image of the peripheral surface of the parts. The composite image is, in turn, processed to optically inspect the parts which may be received and supported on a transfer mechanism which moves the parts between loading, unloading, and inspection stations. At the inspection station the parts have a predetermined position and orientation for the optical inspection.

Figure 3:
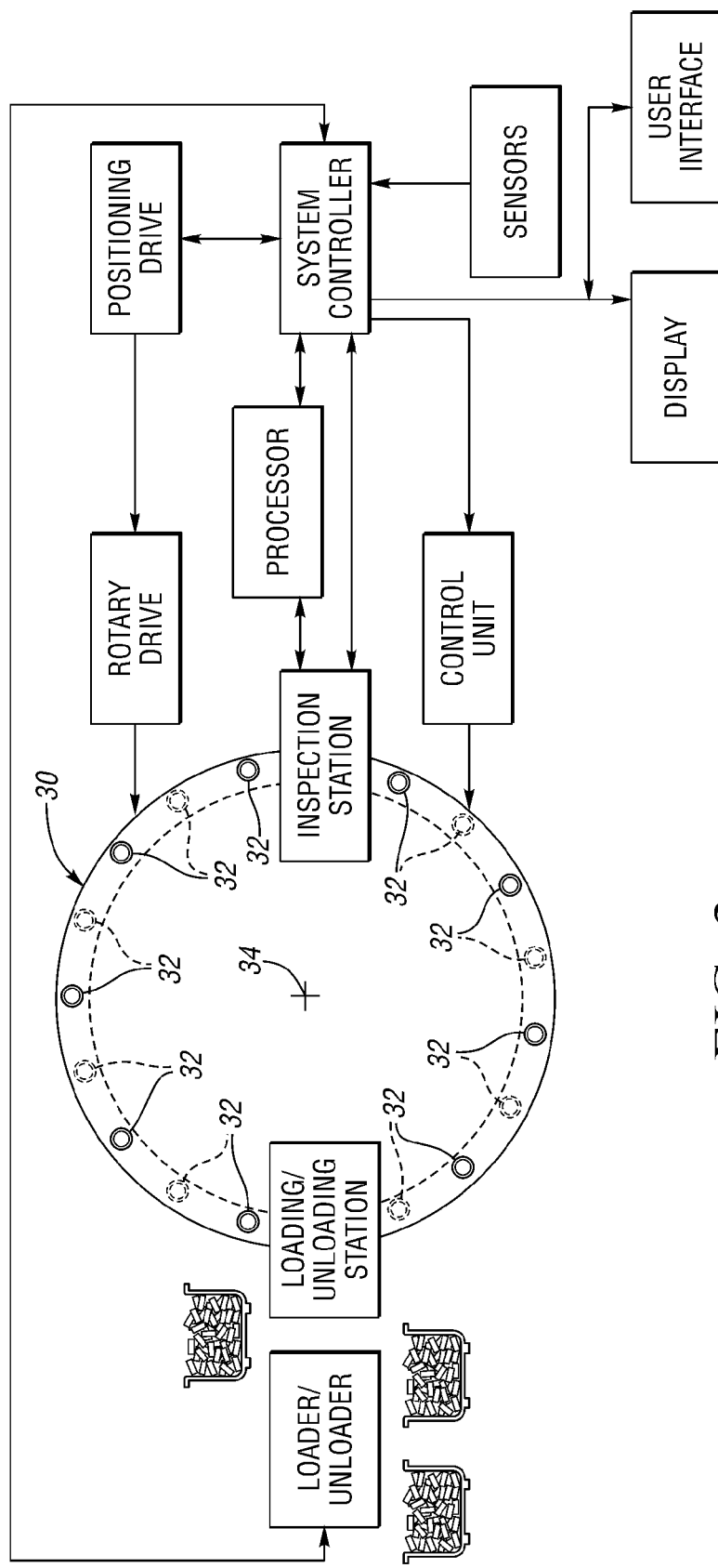
FIG. 3 is a block diagram schematic view of an example embodiment of a system of the invention at inspection, loading and unloading stations.
Figure 4A:
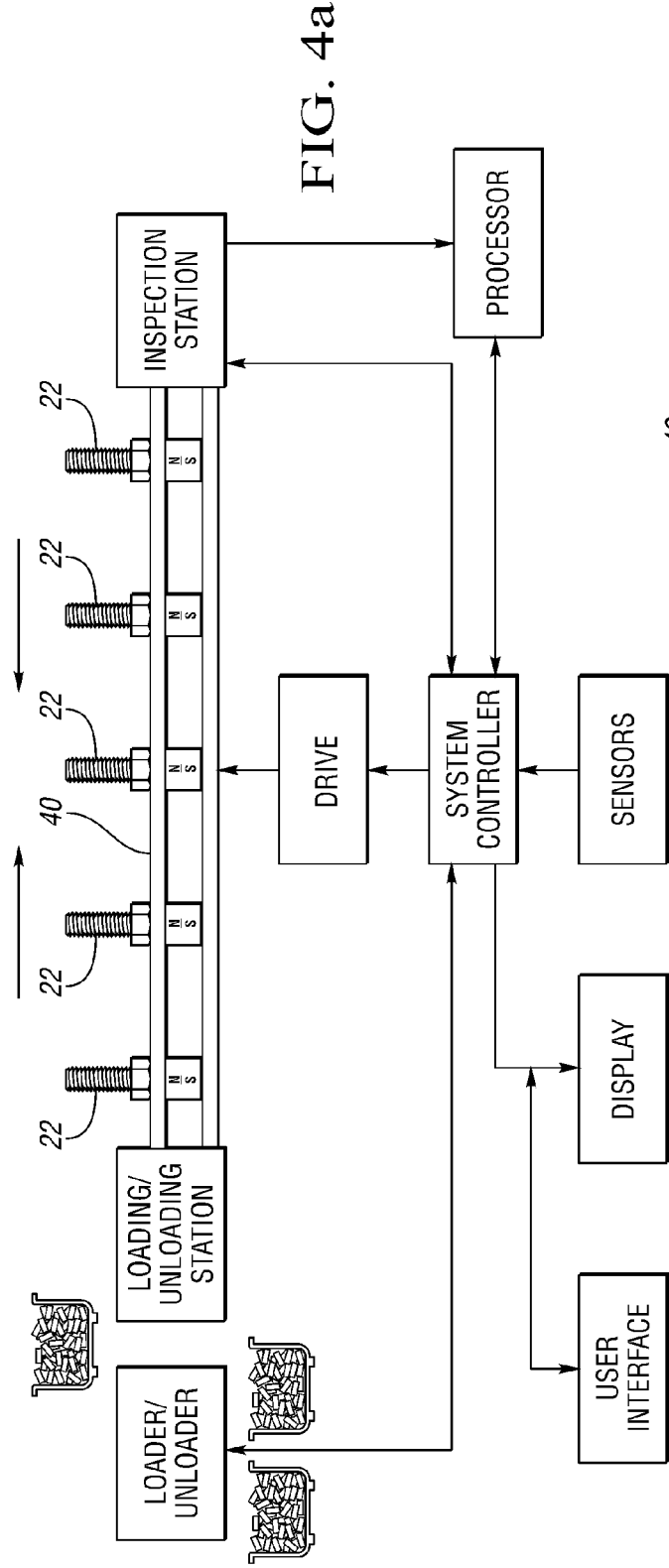
FIG. 4a is a block diagram schematic view of another example of a system of the invention at inspection, loading and unloading stations.

Referring now to FIGS. 3 and 4a, there are illustrated two different examples or embodiments of systems for optically inspecting parts such as ammunition cases or cartridges (FIG. 3) and threaded fasteners (FIG. 4a). Each of the systems of FIGS. 3 and 4 include, a part transfer subsystem including a transfer mechanism (30 in FIG. 3, 40 in FIG. 4a) adapted to receive and retain parts thereon at a loading station at which a loader loads parts to be inspected from a bin or other storage or transfer device. The transfer mechanism 30 or 40 then transfers the retained parts so that the parts travel along a first path which extends from the loading station to an inspection station at which the parts have a predetermined position and orientation for inspection. Subsequently, the transfer mechanism 30 or 40 transfers the parts after inspection at the inspection station so that the inspected parts travel along a second path which extends from the inspection station to an unloading station at which the inspected parts are unloaded from the transfer mechanism 30 or 40 by an unloader. The loader and unloader may be the same device, such as a robot having vision capabilities, which can place parts which "pass" the inspection in a "good part" bin and place parts which don't "pass" the inspection in a "defective part" bin. The unloading station may be coincident with the loading station and the loading and unloading may be done manually or automatically.

As illustrated in FIGS. 3 and 4a, the transfer mechanism 30 may be a rotating table or disk to transfer cases and the transfer mechanism 40 may include a conveyor such as a magnetic or vacuum conveyor for transferring parts such as threaded fasteners such as bolts 22 or screws. Magnetic conveyors are frequently used to convey ferromagnetic articles, such as cans, stampings and the like. In conveyors of this type, permanent magnets are located in the frame of the conveyor beneath the conveying run of an endless belt and articles are attracted to the magnets so that the belt can travel along an incline or vertical path of travel without the articles falling from the belt.

Alternatively, the transfer mechanism 30 can be modified to receive and retain threaded fasteners and the transfer mechanism 40 can be modified to receive and retain cartridge cases. The cartridge cases may be ferromagnetic or, if not ferromagnetic, magnets may be placed in the cases.

Alternatively, an indexing, beltless magnetic conveyor may be provided. Such a conveyer may include a housing defining a longitudinal length of the conveyor and a magnetic rack assembly moveably supported in the housing. The magnetic rack assembly includes a plurality of magnet assemblies supported at spaced intervals relative to one another along the longitudinal length of the conveyor. The beltless magnetic conveyor also includes a drive which is controlled by the system controller to index the magnetic rack assembly between a home or loading position proximate to one end of the housing and an end or inspection position which is proximate to an opposite end of the housing over the same path. The magnet assemblies are operable to generate a magnetic force which acts to attract ferromagnetic material toward the housing and to move the ferromagnetic material in the direction of the longitudinal length of the conveyor when the magnetic rack assembly is indexed.

As further illustrated in FIG. 3, the movable table or disk 30 may be a rotary index table or disk, for transferring parts such as ammunition cases or cartridges 32 either at the top or bottom surfaces of the table 30. The rotary index table 30 typically has a central rotational axis 34 and an outer periphery which has a round shape. A rotary drive of the table is illustrated in FIG. 3 and operates to rotate the index table 30 on a base for indexing rotation about the rotational axis 34 based on various sensor input signals from sensors to a system controller which, in turn, provides sequential control signals to a positioning drive mechanically coupled to the rotary drive. The system controller also provides control signals to a computer display, a part loader/unloader (for example, a robot) and to a control unit which moves the rotary table 30 vertically in relation to its base so that the rotary drive can drive the index table 30 between stations. After the table 30 has moved to the desired station, the control unit controllably lowers the rotary table 30 back onto its base.

Figure 4C:
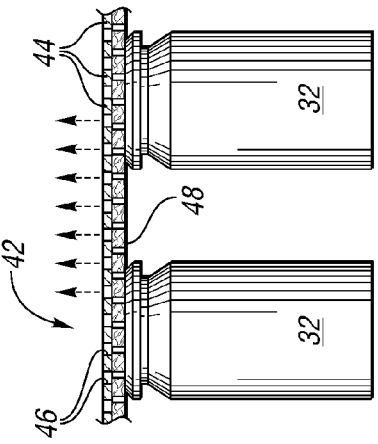
FIG. 4c is a side view, partially broken away and in cross section, of a conveyor belt of a vacuum transfer conveyor wherein heads of parts such as cartridge cases are held against a bottom surface of the perforated belt.
Figure 4B:
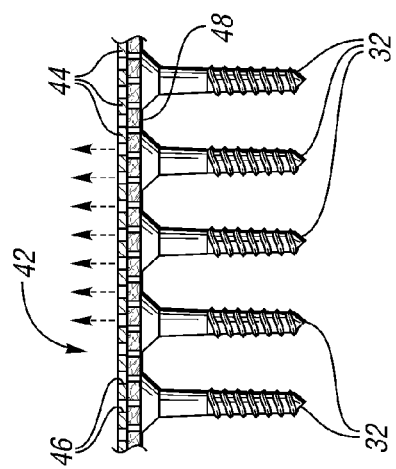
FIG. 4b is a side view, partially broken away and in cross section, of a conveyor belt of a vacuum transfer conveyor wherein heads of parts such as screws are held against a bottom surface of a perforated belt.

Also, alternatively, as illustrated in FIGS. 4b and 4c, the part transfer subsystem may include a vacuum transfer conveyor having a conveyor belt wherein parts, such as screws 32 (FIG. 4b) or cartridge cases 32 (FIG. 4c) are hung or held from their heads to enable lateral optical inspection of the parts. Such parts may include brass cartridge cases, stainless steel fasteners (such as screws) and titanium parts. Typically, such vacuum belt conveyors are capable of transferring small parts or articles between stations while maintaining a predetermined upright position of the part. Such conveyors or conveyor apparatus typically include a vacuum plenum 42, or mechanism for obtaining a vacuum in the plenum 42, a plurality of spaced air openings in a plenum wall 44 as well as an apertured vacuum transfer belt 48 having a reach mounted for movement along an outer surface of the plenum wall 44. The holes in the vacuum conveyor are spaced at intervals to provide a "metering effect" which allows the proper spacing for inspection and rejection of defective parts.

Referring now to FIG. 5, there is illustrated a first embodiment of an illumination assembly in the form of a plurality of LED emitters or fluorescent lamps or bulbs to simultaneously illuminate a plurality of exterior side surfaces of the part such as the cartridge cases 32 supported on the table 30. The side surfaces are equally angularly spaced about the axis of the case 32 and are illuminated with a plurality of separate beams of radiation when the case 32 is located at the inspection station. The lamps may be mounted within an opaque enclosure or housing 60 to minimize extraneous light and shadows and to provide relative uniform lighting within the enclosure.

The illumination assembly may include pulsed or strobed sources of radiation such as LED emitters which are controlled by the system controller. Each LED emitter may include one or more LED's to enhance the imaging of the surfaces of the case 32 so that defects can be easily "seen."

Each lens and detector assemblies typically includes a camera mounted within the enclosure 60, which may be a digital CCD camera (e.g.; color or black/white) and an associated frame grabber (or digital frame buffer provided with the camera), which digitizes the video output from the television camera to obtain pixel data representing a two-dimensional image of the three-dimensional side surfaces of the case 32. The pixel data are stored in a memory of the frame grabber, or transmitted, for instance, by a high speed link, directly to the processer of FIGS. 3, 4 and 5.

The detected optical images are processed by the image processor to obtain a continuous, seamless, 360 degree panoramic composite image which is used by the processor to determine at least one of a dent, a split, a perforation, a crack, a scratch, a wrinkle, a buckle, a bulge, and a surface blemish located at the side surfaces of the case 32.

The system of FIG. 5 is an integrated system designed to fully inspect and measure parts from their sides without any need for part rotation at the inspection station. The system of FIG. 5 can inspect parts which are supported to stand upright or which can be suspended or supported from their heads.

Four, partially overlapped, views of the part are simultaneously provided. The optical path is designed so that the displacement angle between the views is almost exactly 90°. This optical layout ensures complete coverage of the case's lateral surfaces. The optical path is the same for all four viewpoints. Furthermore, such imaging makes the system insensitive to case decentering and therefore suitable for measurement applications. The system is the solution for inspecting parts, such as cases, whose features would be hidden when looked at from the top and for all those applications where a part must be inspected or measured from different sides without part rotation.

Each camera has the image plane which can be, for example, an electronic sensor (CCD, CMOS). Preferably such camera is a high resolution digital telecamera, having the electronic sensor with individual pixels of lateral dimensions equal to or less than one or more microns.

Figure 7:
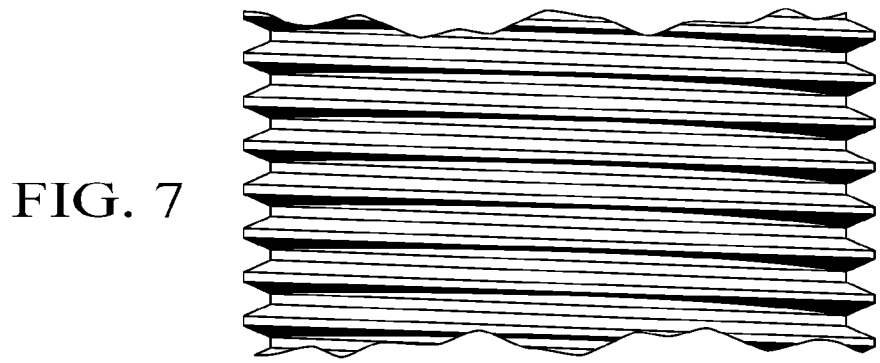
FIG. 7 is a schematic view, partially broken away, of a continuous, seamless, 360 degree panoramic composite image formed by processing a plurality of separate detected optical images.

FIG. 7 is a schematic view of a continuous, seamless, 360 degree panoramic composite image formed by processing a plurality of separate detected optical images. For example, each "curved" 3-D image is "flattened" to obtain a 2-D image using a conventional image processing algorithm. Then the "flattened" images are "stitched" or joined together by another conventional image processing algorithm to form the composite image.

Figure 11:
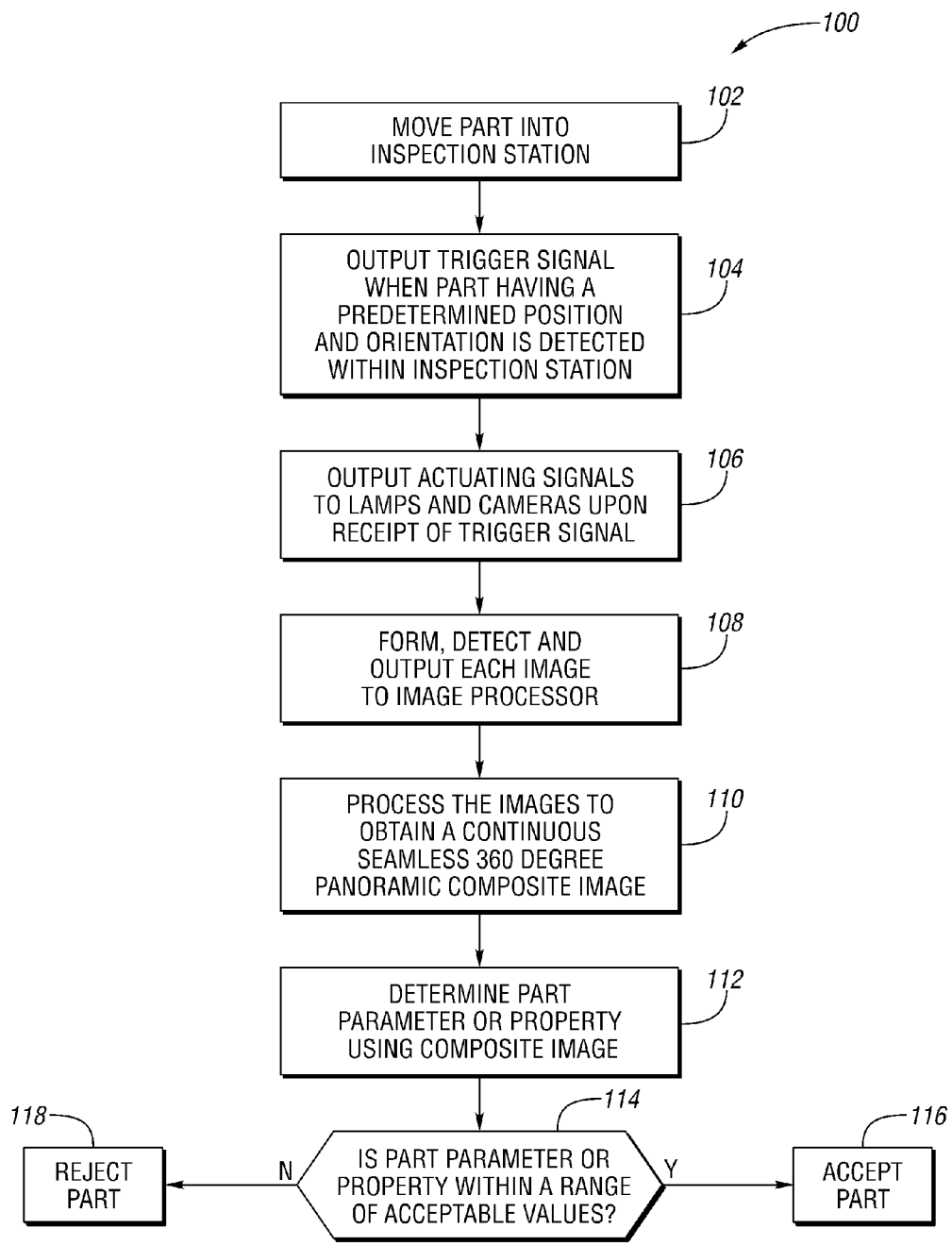
FIG. 11 is a block diagram flow chart illustrating a method of optically inspecting the outer peripheral surfaces of parts in accordance with at least one embodiment of the invention.

FIG. 11 is a detailed block diagram flow chart describing a method of at least one embodiment of the present invention, generally indicated at 100, as follows:

1. Move part into inspection station (block 102);
2. Output trigger signal when part having a predetermined position and orientation is detected within inspection station (block 104);
3. Output actuating signals to lamps and cameras upon receipt of trigger signal (block 106);
4. Form, detect and output each image to image processor (block 108);
5. Process the images to obtain a continuous seamless 360 degree panoramic composite image (block 110);
6. Determine part parameter of property using composite image (block 112);
7. Is part parameter or property within a range of acceptable values? (block 114);
8. If block 114 is "yes" accept part (block 116); and
9. If block 114 is "no" reject part (block 118).

Data/Image Processor for the Detection of Surface Defects on Small Manufactured Parts This vision system is especially designed for the inspection of relatively small manufactured parts such as threaded fasteners and small and medium caliber ammunition. The processing of images of the cartridge cases to detect defective cases is generally described in issued U.S. Pat. No. 7,403,872 as follows with regard to a composite image.

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the camera aperture. Light which reflects off a dented region will not reflect bright background. Alternatively, the light source can be positioned with a shallower angle to the part. This will result in a low background illumination level with dents appearing as well deemed origin spots on the image.

The vision system detects dents on parts with multiple tapered sections. In particular, a bright background is created in highly tapered regions (with dents appearing as dark spots) while a dim background is created in flatter regions (with dents appearing as bright spots).

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is essentially at a pre-defined location and orientation when the images are acquired, the software need not auto-locate the part and identify regions of interest using preset visual clues.

Defect detection in each region of interest is typically conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Previously locating the part in the composite image may be accomplished by running a series of linear edge detection algorithms. This algorithm uses variable threshold, smoothing and size settings to determine the boundary between a light and dark region along a defined line. These three variables are not generally available to the user, but are hard-coded into the software, as the only time they will generally need to change is in the event of large scale lighting adjustments.

The software first uses the above edge detection algorithm to find the back (left) end of the part in the image.

Once the left edge of the part has been located, the software runs four more edge searches along the top and bottom edges of the part.

Once the top and bottom edges of the part have been located, the midpoints of the edge pairs are calculated and joined in order to find the centerline.

The centerline search is then performed again, but rather than conducting the linear edge detections in the vertical direction, they are conducted perpendicular to the newly found centerline. This iteration reduces the small angle error associated with any potential misalignment of the part in the field of view.

A new centerline found using the results of the repeated top and bottom edge search.

Finally, the left edge is again located, this time along the new centerline. This action locates the very center of the left-hand edge of the part.

Part Regions

Figure 8:
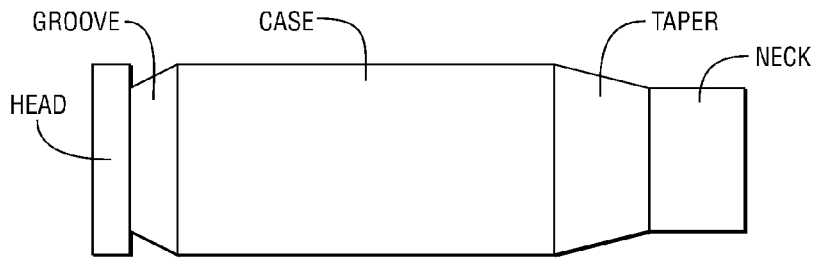
FIG. 8 is a schematic view wherein a framework in the illustrated figure is applied to a part such as a cartridge case once it has been located.

Once the part has been located in the composite image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile. FIG. 8 shows the definition of the various regions on the part.

Figure 9:
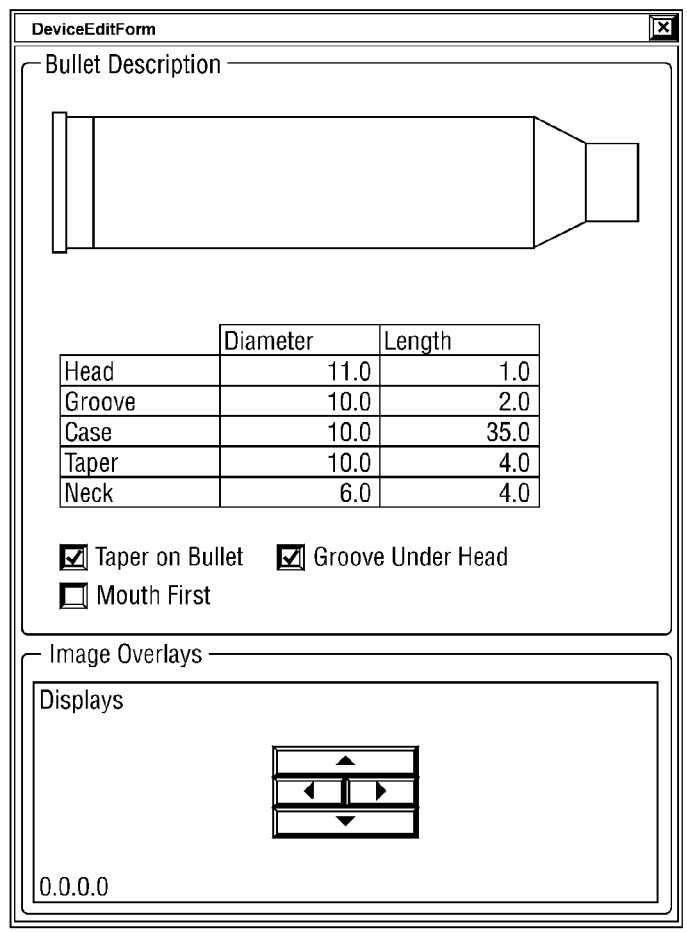
FIG. 9 is a schematic view of a screen shot which describes a cartridge case or bullet to be inspected.

This region definition is shown in screenshot of FIG. 9. Note how the diameter of the groove has been set to be the same as the diameter of the case, resulting in a rectangular groove profile, rather than the trapezoid that is more frequently used.

Defect Search

Figure 10:
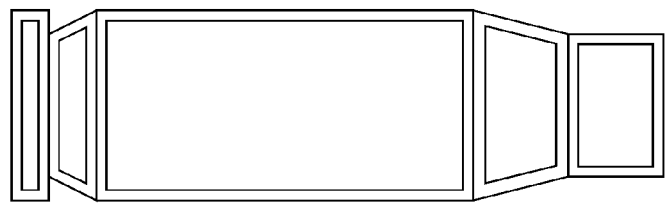
FIG. 10 is a schematic view similar to the view of FIG. 8 wherein buffers are applied once the case regions has been identified.

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile. This concept is demonstrated in FIG. 10.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.

1. Logarithm: Each, pixel brightness value (0-255) is replaced with the log of its brightness value. This serves to expand the brightness values of darker regions while compressing the values of brighter regions, thereby making it easier to find dark defects on a dim background.

2. Sobel Magnitude Operator: The Sobel Operator is the derivative of the image. Therefore, the Sobel Magnitude is shown below:

$$S_M = \sqrt{\left(\frac{\partial f}{\partial x}\right)^2 + \left(\frac{\partial f}{\partial y}\right)^2}$$

although it is frequently approximated as the following:

$$S_M = \frac{\frac{\partial f}{\partial x} + \frac{\partial f}{\partial y}}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.

3. Invert Original Image: The original image captured by the camera is inverted so that bright pixels appear dark and dark pixels appear bright. This results in an image with dark defect areas appearing as bright spots.

4. Multiplication: the image obtained after step 2 is multiplied with the image obtained after step 3. Multiplication of two images like this is functionally equivalent to performing an AND operation on them. Only pixels which appear bright in the resultant image. In this case, the multiplication of these two images will result in the highlighting of the rings found in step two, but only if these rings surround a dark spot.

5. Threshold: All pixels with a brightness below a specified value are set to OFF while all pixels greater than or equal to the specified value are set to ON.

6. Fill in Holes: The image obtained after the completion of steps 1-5 appears as a series of ON-pixel rings. The final step is to fill in all enclosed contours with ON pixels.

After completing these steps, the resultant image should consist of a pixels corresponding to potential defects. These bright blobs are superimposed on areas that originally contained dark defects.

Bright Defects

The detection of bright defects is a two-step process.

1. Threshold: A pixel brightness threshold filter may be applied to pick out all saturated pixels (greyscale255). A user-definable threshold may be provided so values lower than 255 can be detected.

2. Count Filter: A count filter is a technique for filtering small pixel noise. A size parameter is set (2, 3, 4, etc) and a square box is constructed whose sides are this number of pixels in length. Therefore, if the size parameter is set to 3, the box will be 3 pixels by 3 pixels. This box is then centered on every pixel picked out by the threshold filter applied in step 1. The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any "speckling" type noise in the original image which would have results in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold.

Thread Signal/Data Processing

Introduction

What follows is a description of a thread parameter estimation process. This process which is described in general in published U.S. patent application 2010/0238435 provides one embodiment of a standard thread measurement "feature" in the method and system of the invention.

Thread Signal Processing

Thread signal processing is the process of estimating the following thread parameters.

1) pitch
2) major diameter
3) minor diameter
4) functional diameter
5) lead deviation
6) pitch diameter As the thread signal processing proceeds, a number of intermediate data products are produced in early processing stages that are further analyzed in later stages. These include:

rough pos/neg crossing locations
rough crest locations
wire position search intervals
left/right flank lines
wire positions
precise crest/root locations
3-crest average/median measurements of major diameter, minor diameter, pitch diameter
3-D crest cylinder axis
wire position projections on the 3-D crest cylinder axis
3-D crest cylinder diameter
3-D crest root-mean-square distance between crest data and fit.

These intermediate data products are analyzed to produce final estimates of the thread parameters. For example major diameter is estimated as twice the radius of the 3-D crest cylinder. The 3-D crest cylinder axis then depends on the precise crest/root locations. The crest/root locations then depend on the search intervals based on rough crest locations and pos/neg crossings, and on data from the original calibrated part data.

Processing Restrictions
Inspection Region

The thread processing occurs between position limits called an inspection region. In template editor, the user specifies the inspection region by manipulating the upper and lower stage position limits, overlaid on an image of the part.

These limits utilize the calibrated sensor position so that measurements by are aligned to the approximately similar physical positions on the part.

The estimation of thread parameters is specified to be an average estimate over all the data within which the inspection region. In practice, some of the intermediate data products are estimated outside of the inspection region in order to allow estimation of all thread parameters within the full region. For example, a wire position within the inspection region may require a thread crest outside the inspection region.

Measurement Assumption for the Inspection Region

The following requirements guide the user's placement of the inspection region on the image of the part.

The first assumption is that the thread parameters be constant throughout the inspection region. This enables the software to average the estimates from different positions within the inspection region and not be concerned with partitioning or segmenting the data into different regions for special processing.

This requirement excludes the following types of data from the inspection region:

the beginning or end of a threaded region, with thread crests less than full height.

a threaded region with a taper.

a threaded region with a notch or extensive damage.

A second assumption is that the inspection region contains at least 4-6 thread pitches. This amount of data is required to construct several of the intermediate data products with the required accuracy.

A third assumption is that the thread be manufactured with a 60-degree flank angle. Thread processing implicitly utilizes this parameter in several places. One of the most direct usages is the conversion of lead deviation into functional diameter.

A fourth assumption is that the thread has a cylindrical cross section. Non-cylindrical threads would require the 3-D peak cylinder to be suitably generalized. Incorrect fit to a non-cylindrical cross section would lead to incorrect lead deviation measures.

A fifth assumption is that the thread has a single helix.

Measurement of the following threaded fasteners are provided:

non-standard thread types, especially self-tapping screws, small threaded regions with 2 or 3 pitches.

Taptite trilobe threaded regions.

Rough Crossings

The thread model describes herein below is a sampled representation of one thread profile, for exactly one pitch. Thread model starts at the midpoint of a rising thread flank and ends one pitch later.

Using a correlation detector the thread model is matched to data within the inspection regions producing thresholded detections within the inspection region, that are called crossings.

Figure 6:
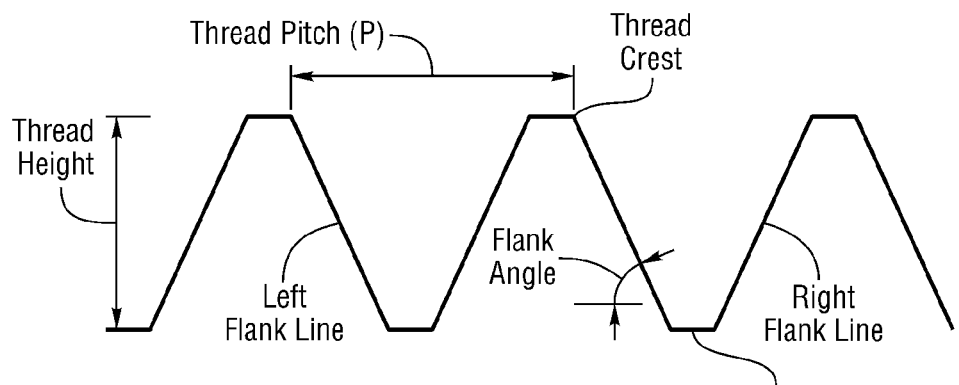
FIG. 6 is a graph wherein a thread profile and its parameters are illustrated.

"Refinements" noted herein may make the crossings more accurate. The refinements also separate the crossings into positive crossings and negative crossings. FIG. 6 illustrates selected concepts of a thread form. The thread model is a lateral sequence of points that represent a best estimate of the outline of one cycle of the thread form.

Rough Crest and Root Positions

A crest/root detector extracts rough crest and root positions between the matched adjacent pairs of positive and negative crossings.

Pitch Estimate

A pitch estimate is required for step set gage wire diameter. The estimate is required to be accurate enough to unambiguously select a unique gage wire from the set appropriate for the measurement. The current process utilizes a two-stage process.

This process may be simplified as described herein.

First Estimate.

Crossing data is analyzed and averaged over all sensors to create a thread pitch estimate, the "crossing pitch."

Second Pitch Estimate

The steps set wire gage diameter, wire position search intervals, measure flank lines and measure 3-point diameters noted herein below are completed in a first iteration. Then the wire positions are averaged over all sensors and positions to compute a pitch estimate.

Set Gage Wire Diameter

Gage wires are utilized in physical thread measurements of pitch diameter in the prior art. Two wires are placed in adjacent threads on one side of the part, and a single wire is placed on the other side of the part. A micrometer measures the distance between the reference line established by the two adjacent gage wires and the reference point established by the other gage wire. A tabulated correction formula converts the micrometer distance to an estimate of the pitch diameter.

Gage wire sizes are thus selected prior to the thread measurement. To do this one estimates the thread pitch as previously described and then one selects the closest gage wire in a set to the pitch estimate. The gage wire set utilized is the one appropriate to the type of measurement; currently there is one set for the metric coarse thread sequence, and another for a similar English thread set. The gage wire sets are chosen at part template edit time by making a selection in a pull down list.

Wire Position Search Intervals

One places "virtual" gage wires onto the calibrated sensor data throughout the inspection region. In order to place the "virtual" gage wires we must identify search intervals for each wire to be located.

A requirement of the following processing steps is that the wire positions in the inspection region have no gaps. Another requirement is that a wire position search interval consist of two valid thread crests, one valid thread root between the two thread crests, and valid positive/negative crossings between the crest/root pairs.

One then searches the set of positive/negative crossings and crest/root positions for the set of wire position search intervals to analyze. The result of intervals, one set per sensor.

Measure Flank Lines

For a left flank all data is analyzed between the rough positions of the left crest and the central root. One then determines the height limits of a flank line data extraction region that covers 70% (a configurable parameter) of the height interval between left crest and central root. This data is extracted into a data set and fit to a line, becoming the left flank line.

The procedure avoids the non-linear regions near the left crest and central root. In addition, a "flank line valid" flag is computed, based on the RMS distance between the left flank line and the data within the left flank line data extraction region. If the RMS distance between the flank line and the data points in the flank line data extraction interval is larger than 10 μm per point (a configurable parameter), then the flag is set to invalid.

The process is repeated for the right flank line and then for all wire position search intervals.

Measure Wire Positions

The wire positions are calculated, given the left and right flank lines and the wire size. The virtual wire is tangent to each flank line and the resulting position is calculated with a simple geometric formula.

The position has a valid flag that is true when both flank lines are valid, and false otherwise.

Measure 3-Point Diameters

The 3-point technique is a method to measure the minor, major, and pitch diameters without explicitly utilizing 3-D information.

For example, consider the major diameter. It is defined as the diameter of a cylinder that contains all the inspection region's thread crests.

In this method, the top of a thread crest in calibrated sensor coordinates forms an elementary measurement. The elementary measurements are combined into triplets for further analysis. Only crests from the two sensors of a single laser are combined.

Two adjacent thread crest positions are combined with the thread crest position that is closest to the average position of crests. The two crests form a reference line. Then the distance from the reference line to the crest is computed. This is the 3 crest distance for that crest triplet.

In this manner, the 3-crest distances from all adjacent crest triplets are computed. The 3-crest distances are all added to a data vector. The 3-crest diameter measurement is either the average or the median of all the 3-crest distances within the 3-crest data vector.

3-Point Minor Diameter

The 3-point minor diameter computes 3-point distances using precise root locations in the sensor data. The 3-point minor diameter is the average of the 3-point distance vector.

3-Point Major Diameter

The 3-point major diameter computes 3-crest distances using precise crest locations in the sensor data. The 3-point major diameter is the median of the 3-point distance vector.

3-Point Wire Pitch Diameter

The 3-point pitch diameter computes 3-point distances using the wire positions computed in the sensor data. The 3-point wire pitch diameter is the median of the 3-pointwire pitch diameter.

FIG. 14 is screen shot from a user interface of a PC which illustrate intermediate data extracted from a M16×1.5 thread plug gage.

Measure 3-D Crest Cylinder

The measured thread crest position data is analyzed to obtain a 3-D cylinder with least squares methods. The 3-D crest cylinder fit has several output parameters of interest.

the RMS distance between the crest position data and the fitted shape.

the 3-D location of the cylinder's central axis.

the radius of the cylinder

Project Wire Positions onto 3-D Crest Cylinder Axis

Measured wire positions can be combined with the 3-D location of the 3-D crest cylinder's central axis. An imaginary disk, perpendicular to the cylinder axis that goes through the measured wire position marks a position on the 3-D crest cylinder axis.

A data set consisting of the projections of all sensor wire positions is constructed.

The output intermediate data is a vector, sorted from minimum to maximum sensor stage position of the projected wire positions.

Thread Parameter Estimation

Thread parameter estimation utilizes the intermediate data products and may also correct them based on a model of the measurement, prior to producing a final thread parameter estimate.

Wire Pitch

Thread pitch is estimated from the wire center intermediate data. For each sensor data set the adjacent pairs of wire positions are used to calculate an adjacent wire pitch, one per adjacent wire positions. For all lasers, each wire pitch is added to a wire pitch vector.

The wire pitch estimate is the median of the elements in the wire pitch vector.

Major Diameter

Thread major diameter is typically reported as the diameter of the 3-D crest cylinder.

If the 3-D crest cylinder fit was unsuccessful, the major diameter is estimated in a different way, detailed below. The cylinder fit can fail due to several factors listed here:

part inclined at too great an angle with respect to the stage axis.

thread crest positions do not fit a cylinder, the RMS fit-to-data distance is too large.

When the cylinder fit fails the major diameter is estimated from the 3-point major diameter data. This case is special because a previous condition (cylinder fit) has already failed. In practice, the cylinder fit most often failed when the threaded region was too short or the inspection extended beyond the end of the threaded region.

Because of this bias a simple median of the 3-point major diameter data would typically be too low, most of the good 3-point data was concentrated at the highest measurements. In this case the major diameter estimate is the value such that 20% of the 3-point data is higher and 80% of the 3-point data is lower.

Calibration Correction

Major diameter is also corrected by a final end-to-end calibration of the total system. The reported major diameter is often two low, with bias ranging from −20 μm to 0.

After diameter calibration the system is exposed to a set of measured thread plug gages. One then plots their major diameter bias as a function of diameter and fit a simple segmented line to the bias results. These bias fits then are entered into the system configuration file and are used to correct the measured major diameter with the measured bias.

Minor Diameter

Thread minor diameter is estimated with the 3-point minor diameter distance vector. The minor diameter value is the average of the elements in the distance vector.

Pitch Diameter

Pitch diameter estimation uses two sets of intermediate data products, the wire positions and the 3-D crest cylinder fit.

The pitch diameter estimate calculation is presented in a step-by-step list below:

a) Compute the pitch diameter contact points with the thread flanks by calculating the intersection of the wire shape with the left or right flank lines.

b) Average the left and right points of intersection, and compute the distance (radius) from the average point to the 3-D crest cylinder fit axis. This is the pitch diameter radius for each wire position.

c) Calculate the average value of the pitch diameter radius.

d) Correct each average wire position radius for the part projection angle, using the angle of the 3-D crest cylinder axis to the stage axis, projected into the sensor's coordinate system.

e) Add left and right sensor corrected pitch diameter radius estimates to product an estimate of the pitch diameter for each view.

f) Average the laser estimates to produce the system pitch diameter estimate.

Correction for Part Projection Angle

The computation of pitch diameter is complicated by projection effects. The light performs an almost perfect orthographic (shadow) projection of the thread's shape. However, the projection is not the same thing as the thread cross section, which is specified in thread design documents. The cross section is the thread shape if it were cut by a plane going through the thread's central axis.

The difference is caused by the thread lead angle, which is in the range of 1-3 degrees for many typical threads. The lead angle means that the thread cross section is most accurately viewed in shadow when the viewing direction coincides with the direction of the lead.

It is impossible to position the thread so that a shadow view of the thread is simultaneously aligned with the top and bottom threads. For the example of a thread with a 3 degree lead angle, tilting the thread to align the top of the thread with the viewing angle will make the angle between the lead and the viewing angle for the bottom thread about 6 degrees.

A correction factor was developed for this effect. If one knows to tilt of the thread with respect to the viewing angle then you can correct the observed pitch diameter radius for the expected bias caused by the projection angle. This correction is precomputed and stored in a table.

For each view the tilt of the thread with respect to the viewing angle can be obtained from the 3-D cylinder fit axis. Separate corrections are applied for the different views.

Calibration Correction

Pitch diameter is also corrected by a final end-to-end calibration of the total system. The reported pitch diameter is often too high, with bias ranging from +5 μm to +35 μm.

After diameter calibration, one exposes the system to a set of measured thread plugs gages. One then plots their pitch diameter bias as a function of diameter and fit a simple segmented line to the bias results. These bias fits then are entered into the system calibration file and are used to correct the measured pitch diameter with the measured bias.

Lead Deviation

The lead deviation estimate uses the wire pitch and the locations of the wire positions as projected onto the 3-D cylinder fit axis.

For an ideal helical thread, the wire position projections should result in a regular pattern along the 3-D cylinder fit axis. Lead deviation is the deviation of that pattern from the ideal, measured as a maximum distance of any projected wire position from the ideal pattern.

The computation of the lead deviation estimate follows a step-by-step procedure:

a) Create a wire position projection vector, containing all the data.

b) Sort the wire position projection vector in order of position along the 3-D cylinder fit axis.

c) Convert the wire positions of the elements of the vector into degrees, by multiplying by the factor (360/pitch) and then reducing the element values modulo 360.

d) Calculate an offset value so that the maximum absolute value of the degree-valued element positions is minimal. For example with a lead deviation of 0.010 mm for a 1 mm pitch thread, the absolute value of at least one degree value element position would be 3.60 degrees (0.010) mm/1 mm equals (1/100) and 360/100 is 3.60)

Convert the value from degrees to mm and report as the lead deviation estimate.

All lead deviation estimates are positive.

Calibration Correction

Errors in measurement mean that the physical measurement of a perfect thread will have a positive lead deviation.

To attempt to correct for this effect, one measures the lead deviation for a set of thread plug gages and plotted them as a function of gage diameter. The most common form observed is a constant lead deviation of 0.010 mm to 0.20 mm.

This value observed in calibration with thread gages is taken to be a bias. This amount of bias is entered into the system calibration file and used to correct the measured lead deviation for this measurement bias.

Functional Diameter

Functional diameter is currently defined in practice by the fit of a special fit gage over the thread. The special fit gage is essentially a nut that is split in two by a plane cut through the central axis of the nut. The two halves of the fit gage are held in a fixture that measures the distance between the two halves. There is one special fit gage for every thread type.

Functional diameter is defined as the pitch diameter when the special fit gage is clamped tightly over a thread plug setting gage. When one puts a different part into the fit gage the fit gage may expand slightly, due to a summation of effects involving the differences between the part and the thread plug setting gage used to setup the functional diameter measurement. The functional diameter measurement is then the thread plug setting gage's pitch diameter plus the additional separation between the two fit gage pieces.

Functional Diameter Estimator

The functional diameter measurement method is an approximation of the fit gage method. We do not perform a full 3-D analog of the physical fit gage. Instead we have made an approximation that involves the use of lead deviation and the shape of the thread form.

If we imagine the thread form as perfect and also having a 60 degree flank angle then lead deviations should cause the thread form fit gage pieces to move apart. A single lead deviation either up or down the thread form axis will cause a single split piece of the fitting gage to move outward. The amount of outward movement for a 60 degree flank angle will be equal to ($\sqrt{3}$) (lead deviation). The movement provides a clearance for both positive and negative movements of the lead, relative to a perfect helical shape.

$$FD = PD + \sqrt{3}(\text{LeadDeviation})$$

Learning the Thread Model

The thread model is a learned sequence of points that represent a best estimate of the outline of one cycle of the thread form. The thread model is calculated when the inspection region is specified, at template edit time.

The measure template routine uses a pattern match algorithm with a sine wave pattern to identify periodically in the inspection region data. This process determines an approximate thread pitch. The process also calculates a starting point in the data vector for the first beginning of the matched pattern, which is an approximation to the first midpoint of a right flank line.

With the pitch and the starting point in hand, the measure template routine can then calculate an average thread model. Starting with the first sample point in the matched pattern, points that are 1, 2, 3, . . . , N pitches later in the inspection region are averaged to form the first point of the thread model. The process is repeated for all the rest of the points in the first matched pattern. The thread model is then stored in the template for later use.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of optically inspecting parts, each of the parts having a length, a width, an axis and an outer peripheral surface which extends 360° around the part, the method comprising:
   supporting a part to be inspected at an inspection station so that the part has a predetermined position and orientation for inspection;
   supporting a plurality of angularly spaced radiation sources at the inspection station;
   energizing the radiation sources so that the radiation sources simultaneously illuminate a plurality of exterior side surfaces of the part which are angularly spaced about the axis of the part at the inspection station to obtain corresponding reflected radiation signals;
   forming an optical image of each illuminated side surface from the reflected radiation signals at an image plane;
   detecting the optical images at the image planes to obtain a plurality of detected optical images; and
   processing the detected optical images to obtain a continuous, seamless, 360° panoramic composite image of the peripheral surface of the part.

2. The method as claimed in claim 1 further comprising moving the part relative to the inspection station both prior to and after inspection.

3. The method as claimed in claim 1, wherein the part is substantially stationary during inspection.

4. The method as claimed in claim 2, further comprising the step of coordinating the inspection of the part at the inspection station with the relative movement of the part to and from the inspection station to control the relative movement and the inspecting of the part.

5. The method as claimed in claim 1, further comprising processing the composite image to identify a defective part.

6. The method as claimed in claim 1, further comprising processing the composite image to obtain a measurement of the part.

7. The method as claimed in claim 1, wherein the radiation sources are visible light sources.

8. The method as claimed in claim 1, wherein the radiation is LED or fluorescent radiation.

9. The method as claimed in claim 1, wherein the parts include cartridge cases.

10. The method as claimed in claim 9, further comprising processing the composite image to determine at least one of a dent, a split, a perforation, a crack, a scratch, a wrinkle, a buckle, a bulge, and a surface blemish located at the side surfaces of the case.

11. The method as claimed in claim 1, wherein the parts include threaded fasteners.

12. The method as claimed in claim 11, further comprising processing the composite image to determine a thread profile parameter.

13. The method as claimed in claim 11, further comprising processing the composite image to identify a thread defect.

14. A system for optically inspecting parts, each of the parts having a length, a width, an axis and an outer peripheral surface which extends 360° around the part, the system comprising:
   an enclosure which allows movement of a part relative to the enclosure both prior to and after inspection within the enclosure;
   an illumination assembly to simultaneously illuminate a plurality of exterior side surfaces of the part which are annularly spaced about the axis of the part with radiation when the part is at a predetermined location within the enclosure to obtain corresponding reflected radiation signals;
   a plurality of lens and detector assemblies forming an optical image of each illuminated side surfaces from the reflected radiation signals at an image plane, each of the assemblies forming an optical image of one of the illuminated exterior side surfaces from the reflected radiation signals and detecting the formed optical image within the enclosure; and
   a processor to process the detected optical images to obtain a continuous, seamless, 360° panoramic composite image of the peripheral surface of the part.

15. The system as claimed in claim 14, further comprising a part transfer subsystem to transfer the part so that the part travels along a first path which extends into the enclosure and to transfer the part after inspection so that the inspected part travels along a second path which extends out of the enclosure.

16. The system as claimed in claim 14, wherein each of the lens and detector assemblies includes an image sensor having an image plane to detect optical images.

17. The system as claimed in claim 14, wherein the radiation is LED or fluorescent radiation.

18. The system as claimed in claim 14, wherein the parts include cartridge cases.

19. The system as claimed in claim 18, wherein the processor processes the composite image to determine at least one of a dent, a split, a perforation, a crack, a scratch, a wrinkle, a buckle, a bulge, and a surface blemish located at the side surfaces of the case.

20. The system as claimed in claim 14, wherein the parts include threaded fasteners.

21. The system as claimed in claim 20, wherein the processor processes the composite image to identify a thread profile parameter.

22. The system as claimed in claim 20, wherein the processor processes the composite image to identify a thread defect.

23. The system as claimed in claim 15, wherein the part transfer subsystem includes a conveyor.

24. The system as claimed in claim 15, wherein the part transfer subsystem includes a movable table or disk.

* * * * *

UNITED STATES PATENT AND TRADEMARK OFFICE
CERTIFICATE OF CORRECTION

| | | |
|---|---|---|
| PATENT NO. | : 9,047,657 B2 | Page 1 of 1 |
| APPLICATION NO. | : 13/873293 | |
| DATED | : June 2, 2015 | |
| INVENTOR(S) | : Michael Nygaard | |

It is certified that error appears in the above-identified patent and that said Letters Patent is hereby corrected as shown below:

On the Title Page

Delete:

"(73)   Assignee:       GII ACQUISITION, LCC, Davisburg, MI (US)"

and insert:

--(73)   Assignee:       GII ACQUISITION, LLC, Davisburg, MI (US)--

Signed and Sealed this
Third Day of November, 2015

Michelle K. Lee
*Director of the United States Patent and Trademark Office*